(12) United States Patent
Nishio

(10) Patent No.: US 8,030,338 B2
(45) Date of Patent: Oct. 4, 2011

(54) METHOD FOR PRODUCING 2-NITROIMIDAZOLE DERIVATIVE

(75) Inventor: Azuma Nishio, Yokohama (JP)

(73) Assignee: Pola Pharma Inc., Tokyo (JP)

( * ) Notice: Subject to any disclaimer, the term of this patent is extended or adjusted under 35 U.S.C. 154(b) by 107 days.

(21) Appl. No.: 12/522,926

(22) PCT Filed: Jan. 17, 2008

(86) PCT No.: PCT/JP2008/000038

§ 371 (c)(1),
(2), (4) Date: Jul. 13, 2009

(87) PCT Pub. No.: WO2008/090731

PCT Pub. Date: Jul. 31, 2008

(65) Prior Publication Data

US 2010/0004460 A1    Jan. 7, 2010

(30) Foreign Application Priority Data

Jan. 23, 2007 (JP) .................. 2007-012147

(51) Int. Cl.
  *A61K 31/4168* (2006.01)
  *C07D 233/28* (2006.01)

(52) U.S. Cl. ..................... 514/398; 548/327.5

(58) Field of Classification Search ........... 548/327.5; 514/398

See application file for complete search history.

(56) References Cited

U.S. PATENT DOCUMENTS

| | | | |
|---|---|---|---|
| 4,945,102 A | 7/1990 | Suzuki et al. | |
| 5,064,849 A | 11/1991 | Suzuki et al. | |
| 6,743,925 B1 | 6/2004 | Takai et al. | |

FOREIGN PATENT DOCUMENTS

| | | | |
|---|---|---|---|
| JP | 1 110675 | | 4/1989 |
| JP | 2-48549 | | 2/1990 |
| JP | 3-223258 | | 10/1991 |
| JP | 6-228123 | | 8/1994 |
| JP | 06-228123 | * | 8/1994 |
| JP | 6-279415 | | 10/1994 |
| JP | 2003 509413 | | 3/2003 |
| JP | 2005-538030 | | 12/2005 |
| WO | WO 01/97860 A2 | | 12/2001 |
| WO | WO 01/97860 A3 | | 12/2001 |

OTHER PUBLICATIONS

Abstract of Aragozzini et al, "Enatioselective microbial reduction of monoesters of 1,3-dihydroxypropane: Synthesis of (S)-and (R)-1,2-O-isopropylideneglycerol," Synthesis (1989), vol. 3, pp. 225-227.*

Takekuma et al, "Preparation of 1-O-Benzoylglycerol and its Effect on the Formation of the Fruit Body of Tokiirohiratake," Chem. Society of Japan (2001), vol. 1, pp. 61-64.*

Wada, Hiroaki et al., "Synthesis of 1-[2-[$^{18}$F]Fluoro-1-(hydroxymethyl)-ethoxy]methyl-2-nitroimidazole ([$^{18}$FENI), a Potential Agent for Imaging Hypoxic Tissues by PET", Journal of Labelled Compounds and Radiopharmaceuticals, vol. 43, No. 8, pp. 785-793, (2000).

* cited by examiner

*Primary Examiner* — Joseph K. McKane
*Assistant Examiner* — Janet L Coppins
(74) *Attorney, Agent, or Firm* — Oblon, Spivak, McClelland, Maier & Neustadt, L.L.P.

(57) ABSTRACT

It is an object to provide a method for producing a 2-nitroimidazole derivative having an acyclic sugar chain in a side chain, which is suitable for production of a derivative having a radioisotope.

A method for producing 1-(1-benzoyloxymethyl-2-hydroxyethyl)oxymethyl-2-nitroimidazole, characterized by reacting glycerin with a benzoylating agent to obtain 1-O-benzoylglycerin, reacting 1-O-benzoylglycerin with dimethoxymethane in the presence of a dehydrating agent to obtain 4-benzoyloxymethyl-1,3-dioxolane, and then reacting this product with 2-nitroimidazole or 2-nitro-1-trialkylsilylimidazole in the presence of a Lewis acid.

16 Claims, No Drawings

METHOD FOR PRODUCING 2-NITROIMIDAZOLE DERIVATIVE

TECHNICAL FIELD

The present invention relates to a method for producing a 2-nitroimidazole derivative having an acyclic sugar chain structure, and more particularly, to a method for producing 1-(1-hydroxymethyl-2-fluoro)ethoxymethyl-2-nitroimidazole.

BACKGROUND ART

Compounds having 2-nitroimidazole as parent nucleus show high orientation toward hypoxic cancer cells, and have an excellent action of reoxygenating hypoxic cancer cells due to the high electron affinity of the nitro group. Thus, investigations have been extensively conducted on the use of such characteristics in cancer radiotherapy in relation to hypoxic cancers having radiation resistance. Particularly, if a side chain of 2-nitroimidazole has an acyclic sugar chain structure, it is known that the corresponding compounds have features of being easily metabolized and excreted, and being available within cancer cells when exposure to radiation is needed, while being rapidly excreted out of the body after completion of radiation treatment, thus the compounds being highly useful (see, for example, Patent Documents 1 to 3). However, introducing an acyclic sugar chain structure leads to the introduction of a large number of reactive hydroxyl groups, and thus is also accompanied by a demerit such as that a number of processes for protection and deprotection of such hydroxyl groups must be undertaken, and more time is required in the production.

Thereafter, it was also found, as a characteristic of 2-nitroimidazole derivatives, that the derivatives have a property of readily orienting themselves at hypoxic sites, without being limited to cancer sites. Thus, discovery was made on the use of the derivatives as imaging agents for hypoxic sites, by introducing $^{18}F$ as a radioisotope into a side chain of such a derivative, and visualizing the location of presence of the derivative inside the body using positron emission tomography (PET) (see, for example, Patent Documents 4 and 5). However, in the case of introducing such a radioisotope, if the derivative has the previously mentioned acyclic sugar chain structure in the side chain, the operations of protection and deprotection of hydroxyl groups must be repeated, and thus degradation of the compound frequently occurred during the time of such operation, and the final yield was also unavoidably lowered. Upon considering the scarcity value of $^{18}F$, it can be said that circumstances such as described above definitely bring forth large losses.

Meanwhile, in regard to the introduction of an acyclic sugar chain, attempts have been made to bring an improvement even in terms of the difficulty in production (see, for example, Patent Documents 6 and 7), but a method suitable for producing such a derivative having a radioisotope has not yet been found.

[Patent Document 1] JP-A-06-279415
[Patent Document 2] JP-A-03-223258
[Patent Document 3] JP-A-01-110675
[Patent Document 4] Japanese kohyo Patent Publication No.
[Patent Document 5] Japanese kohyo Patent Publication No.
[Patent Document 6] JP-A-02-48549
[Patent Document 7] JP-A-06-228123

DISCLOSURE OF THE INVENTION

Problems to be Solved by the Invention

The present invention was made under such circumstances, and it is an object of the present invention to provide a method for producing a 2-nitroimidazole derivative having an acyclic sugar chain in a side chain, which is suitable for the production of a derivative having a radioisotope.

Means to solve the Problems

In view of such circumstances, the inventors of the present invention devotedly made research efforts to seek for a method for producing a 2-nitroimidazole derivative having an acyclic sugar chain in a side chain, which is suitable for the production of a derivative having a radioisotope, and as a result, they found that when steps of using glycerin as a raw material to selectively benzoylate the 1-position and then converting the resultant to 4-benzoyloxymethyl-1,3-dioxolane, are employed, 1-(1-benzoyloxymethyl-2-hydroxyethyl)oxymethyl-2-nitroimidazole is obtained with a small number of processes, and 1-(1-hydroxymethyl-2-fluoro)ethoxymethyl-2-nitroimidazole can be easily produced from the aforementioned compound. As the result, it was found that a threshold-like time in the production of an imaging agent can be cleared, and the yield can be significantly enhanced, and thus the present invention was completed.

That is, the present invention provides a method for producing 1-(1-benzoyloxymethyl-2-hydroxyethyl)oxymethyl-2-nitroimidazole, characterized in that glycerin is reacted with a benzoylating agent to obtain 1-O-benzoylglycerin, 1-O-benzoylglycerin is reacted with dimethoxymethane in the presence of a dehydrating agent to obtain 4-benzoyloxymethyl-1,3-dioxolane, and then this is reacted with 2-nitroimidazole or 2-nitro-1-trialkylsilylimidazole in the presence of a Lewis acid.

The present invention also provides a method for producing 1-(1-hydroxymethyl-2-fluoro)ethoxymethyl-2-nitroimidazole, characterized in that the 1-(1-benzoyloxymethyl-2-hydroxyethyl)oxymethyl-2-nitroimidazole obtained by the above-described method is subjected to substituted sulfonylation, fluorination, and then debenzoylation.

EFFECTS OF THE INVENTION

The present invention is a method for producing 1-(1-hydroxymethyl-2-fluoro)ethoxymethyl-2-nitroimidazole which is useful for an imaging agent for positron emission tomography (PET), or the like, and the method is characterized by having a process of deriving a monobenzoyl ester from glycerin, subsequently deriving a 1,3-dioxolane derivative therefrom, and ring-opening condensing the product with 2-nitroimidazole in the presence of a Lewis acid, to obtain 1-(1-benzoyloxymethyl-2-hydroxyethyl)oxymethyl-2-nitroimidazole. That is, the present invention is characterized by providing a means for producing 1-(1-hydroxymethyl-2-fluoro)ethoxymethyl-2-nitroimidazole, by employing a process of producing 1-(1-benzoyloxymethyl-2-hydroxyethyl)oxymethyl-2-nitroimidazole, which is an important intermediate for the process of producing 1-(1-hydroxymethyl-2-fluoro)ethoxymethyl-2-nitroimidazole, with the number of processes as small as possible, and thereby suppressing the contents of related substances such as a dihydroxy form or a dibenzoyl form, to be low. By transferring the location of the hydroxyl group of this intermediate onto a fluorine atom, the target compound 1-(1-hydroxymethyl-2- fluoro)ethoxymethyl-2-nitroimidazole is obtained, but if the contents of the aforementioned related substances are large, the proportion of introduction of fluorine is affected. This in turn affects the property of quantitativeness as an imaging agent, and therefore, enhancing the production purity of the intermediate 1-(1-benzoyloxymethyl-2-hydroxyethyl) oxymethyl-2-nitroimidazole serves as an important factor for maintaining product quality.

Therefore, according to the present invention, a nitroimidazole derivative having a radioisotope can be produced at a high yield and in a short time.

BEST MODE FOR CARRYING OUT THE INVENTION

The method of the present invention may be presented in a reaction scheme, as follows.

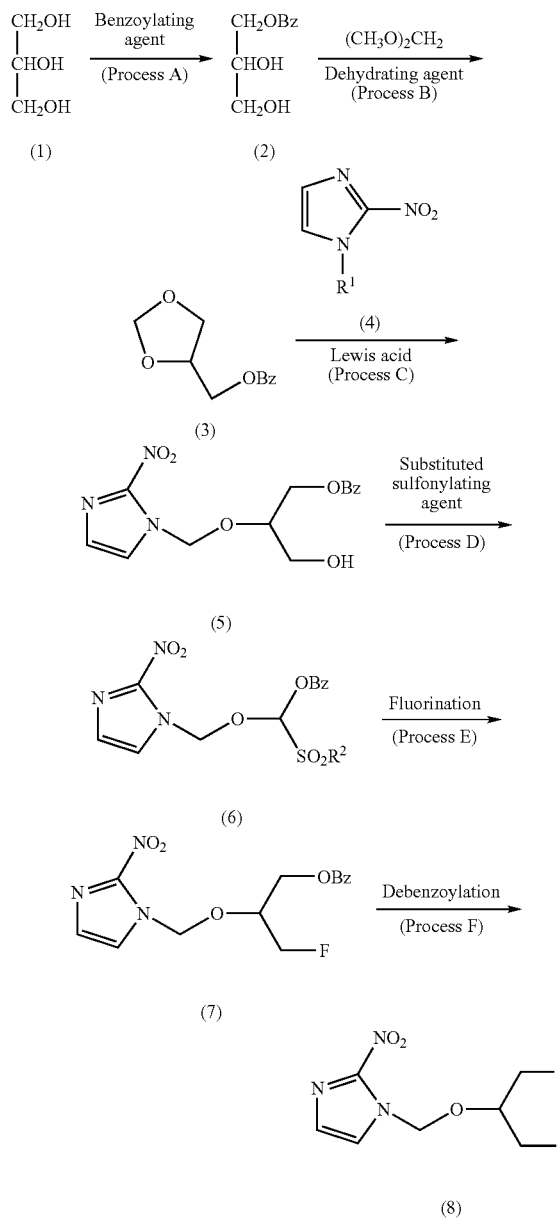

wherein Bz represents a benzoyl group; $R^1$ represents a hydrogen atom or a trialkylsilyl group; and $R^2$ represents a substituent such as an alkyl group or an alkylphenyl group.

The present invention will be described by referring to each of the reaction processes.

Process A

Process A is a process of reacting glycerin (1) with a benzoylating agent to obtain 1-O-benzoylglycerin (2).

As the benzoylating agent, there may be mentioned benzoyl halides, benzoic acid (in the presence of an acid catalyst or a base catalyst) and the like, and among these, benzoyl halides are particularly preferred from the viewpoint that they are capable of acylating only the 1-position. As the halogen atom for the benzoyl halides, a chlorine atom and a bromine atom may be mentioned, but a chlorine atom is preferred. In particular, benzoyl chloride is preferred as the benzoylating agent.

A preferred example of the benzoylation reaction of the process A may involve slowly adding a benzoylating agent to glycerin in the presence of an alkali, while controlling the temperature from ice-coldness to about 60° C. and stirring. The molar ratio of glycerin and the benzoylating agent is preferably a large excess of glycerin, more preferably 5:1 to 1:1, and even more preferably 3:1 to 3:2. Employing the conditions of such alleviation and use of glycerin in excess leads to the preferential introduction of a benzoyl group to the α-position and to the high-yield production of 1-O-benzoylglycerin, which is preferable. As for the solvent, for example, methylene chloride and chloroform are preferred, and it is preferable to use the solvent in at least 10 times the amount of glycerin. As the co-present alkali, for example, an organic amine such as pyridine or triethylamine, and a carbonate such as potassium carbonate may be suitably taken as examples, and it is preferable to use the alkali in an equal amount or a two-fold amount, relative to the benzoylating agent.

The thus-obtained 1-O-benzoylglycerin is preferably purified by performing column chromatography or precision distillation as appropriate, and then subjected to process B.

Process B is a process of reacting 1-O-benzoylglycerin (2) with dimethoxymethane in the presence of a dehydrating agent, to obtain 4-benzoyloxymethyl-1,3-dioxolane (3).

As the dehydrating agent used in the process B, phosphorus pentoxide, p-toluenesulfonic acid, phosphorus oxychloride and the like may be mentioned, but phosphorus pentoxide is particularly preferred. It is preferable to use dimethoxymethane in large excess, for example, in a ten-fold molar amount or more relative to 1-O-benzoylglycerin (2).

The reaction of the process B is preferably performed under water cooling or at room temperature. The reaction time is preferably set to at least 3 hours or more, and preferably 12 to 48 hours. The resulting 4-benzoyloxymethyl-1,3-dioxolane can be easily purified by distillation under reduced pressure or column chromatography.

Process C is a process of reacting 4-benzoyloxymethyl-1,3-dioxolane (3) with 2-nitroimidazole or 2-nitro-1-trialkylsilylimidazole (4) in the presence of a Lewis acid, to obtain 1-(1-benzoyloxymethyl-2-hydroxyethyl)oxymethyl-2-nitroimidazole (5).

Among the 2-nitroimidazole derivatives (4) used in the process, 2-nitro-1-trialkylsilylimidazole is particularly preferred. Here, as the trialkylsilyl group, a tri($C_{1-4}$ alkyl)silyl group such as a trimethylsilyl group or a triethylsilyl group is preferred. This 2-nitro-1-trialkylsilylimidazole is obtained by reacting bistrialkylsilylacetamide, hexaalkylsilazane or the like, with 2-nitroimidazole.

As the Lewis acid used in the process B, stannic chloride, boron trifluoride-ether complexes, aluminum chloride, and the like are suitable.

The amount ratio of 1,3-dioxolane derivative (3) and 2-nitroimidazole derivative (4) is preferably 1:1 to 5:1. The amount of use of the Lewis acid is preferably more or less equivalent to the amount of 2-nitroimidazole (4). In such a reaction, a solvent may also be used, and suitable examples of the solvent include dimethylformamide (may also be referred to as DMF), dimethylsulfoxide (may also be referred to as DMSO), and the like. It is preferable to perform the addition of Lewis acid slowly, and in the case of a liquid Lewis acid such as stannic chloride or boron trifluoride-ether complex, it is preferable to add the Lewis acid dropwise. The relevant reaction can be performed under the temperature conditions of from room temperature to 80° C.

For a comparison of the synthesis route of the present invention as described above and a conventional method, the scheme of a conventional synthesis method will be presented below. In the conventional method, an acetyl group is used as the final protective group, instead of a benzoyl group.

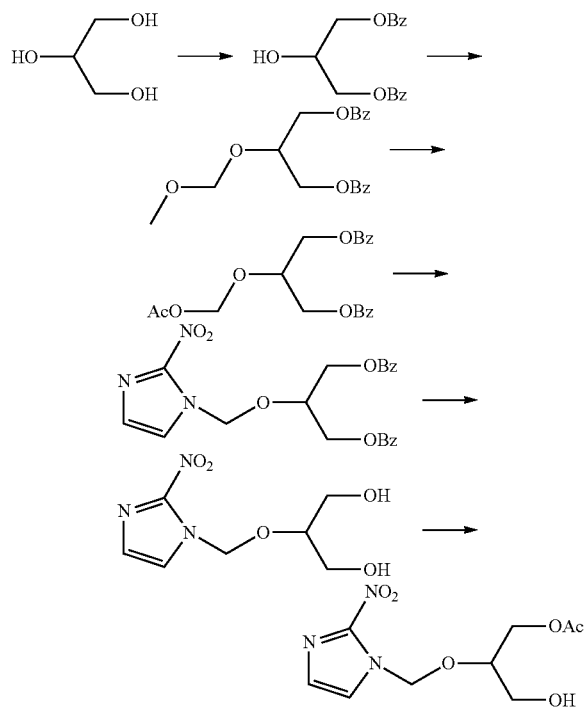

wherein Bz represents a benzoyl group; and Ac represents an acetyl group.

A major difference between the conventional production method and the production method of the present invention is the number of reaction processes, and particularly the number of processes after the introduction of a 2-nitroimidazole skeleton, and since it is required to maintain the production purity of 1-(1-benzoyl (or acetyl)oxymethyl-2-hydroxyethyl) oxymethyl-2-nitroimidazole, a purification process is needed for each step after the introduction of the 2-nitroimidazole skeleton, and therefore the number of purification processes is increased. This results in a decrease in the yield.

A second difference is that upon the introduction of the 2-nitroimidazole skeleton, the present invention involves condensation based on the ring-opening reaction of dioxolane, while the technology of the related art involves a deacetic acid reaction. In this reaction, a reaction concurrently occurs in which the released acetic acid serves as a catalyst so that the produced 1-(1,3-bisbenzoyloxypropan-2-yl)oxy-2-nitroimidazole is decomposed, and 2-nitroimidazole, formalin and 1,3-dibenzoylglycerin are generated, and thus the yield of the target product is decreased. Furthermore, a process for removal of such side products becomes more difficult.

A third difference is that the final protective group is a benzoyl group in the present invention, while it is an acetyl group in the technology of the related art. In a reaction for deriving a monoacetyl form from a dihydroxy form, a diacetyl form and an unreacted form appear to the same extent, thereby decreasing the yield, and there also remains a defect that even if purification is repeated, the degree of separation is low among the monoacetyl form, the diacetyl form and the dihydroxy form, and these derivatives are likely to remain as analogs. Such remaining leads to a decrease in the degree of radioactivation, and there may also occur a situation where repurification or the like is required.

Process D is a process of substituted sulfonylating 1-(1-benzoyloxymethyl-2- Hydroxyethy)poxymethyl-2-nitroimidazole (5). As the substituted sulfonylating agent used in the substituted sulfonylation, an alkylsulfonyl halide such as methanesulfonyl halide, an alkylbenzenesulfonyl halide such as p-toluenesulfonyl halide, and the like may be mentioned. Therefore, as $R^2$ in the compound (6) obtained by this process D, there may be mentioned a $C_{1-4}$ alkyl group such as a methyl group, or a $C_{1-4}$ phenyl group such as a p-toluene group.

The substituted sulfonylation may be carried out according to a conventional method, and may be carried out by, for example, performing the reaction at 0 to 100° C. for 1 to 5 hours, using 2 to 3 moles of a substituted sulfonyl halide (for example, tosyl chloride, or the like) relative to 1 mole of the compound (5), in an organic solvent such as methylene chloride, acetonitrile, dimethylformamide or pyridine in the presence of a base such as triethylamine.

Process E is a process of fluorinating the compound (6).

The fluorination reaction can be carried out in an inert solvent, using a crown ether or the like as a catalyst, and a fluorinating agent such as an alkali metal fluoride (such as, for example, sodium fluoride, potassium fluoride or cesium fluoride), or a tetraammonium fluoride (such as, for example, tetrabutylammonium fluoride). As the inert solvent, a halogen-based solvent, an ether-based solvent, a hydrocarbon-based solvent, a polar solvent, or a mixed solvent of these is preferred. Fluorination is performed usually at about 70 to 130° C., and in the case of using DMF as the solvent, preferably at 100 to 120° C.

In the case of using a $^{18}F$ fluoride (for example, $K^{18}F$) as the fluorinating agent, the fluorination reaction is preferably performed using Kryptofix 2.2.2, which acts as a phase transfer catalyst, or the like. The fluoride source of $^{18}F$ can be obtained by trapping an aqueous solution of $^{18}F$ obtained from a $H_2^{18}O$ concentrated water by $^{18}O$ (p, n.), with an anion exchange resin, and eluting the resultant with an aqueous solution of potassium carbonate.

Process F is a process of debenzoylating the compound (7) to obtain the target compound (8). The debenzoylation reaction is carried out by, for example, a hydrolysis reaction.

The hydrolysis reaction can be performed in a solvent in the presence of an inorganic base, at 0 to 100° C. for 1 to 5 minutes. The inorganic base may be potassium hydroxide, sodium hydroxide, potassium carbonate, sodium carbonate or cesium carbonate. The solvent may be water; an alcohol such as methanol, ethanol or propanol; an ether such as tetrahydrofuran, diethyl ether or dioxane; or a ketone such as acetone or methyl ethyl ketone.

When the thus-obtained nitroimidazole derivative (8) is administered into a living body, the derivative distinguishes an ischemic site or cancer cells, and rapidly orients itself toward these, and therefore, the derivative is useful as an agent for diagnostic imaging, and can detect the location of presence of an ischemic site or cancer cells when used together with a diagnostic imaging apparatus such as MRI, making it possible to measure the amount of the site or the cells.

Hereinafter, the present invention will be described in more detail by way of Examples, but it is needless to say that the present invention is not limited only to such Examples.

EXAMPLES

Reference Example 1-(1-Acetyloxymethyl-2-hydroxyethyl)oxymethyl-2-nitro imidazole was produced according to a conventional method. That is, 9.2 g of glycerin was dissolved in 100 ml of chloroform, 50 ml of triethylamine was added thereto, and under ice cooling, 30 g of benzoyl chloride was dissolved in 50 ml of chloroform and added dropwise to the above-obtained mixture while stirring. After completion of the dropwise addition, the mixture was returned to room temperature, and stirring was continued for one hour at room temperature. The mixture was washed with 100 ml of water, and then the mixture was concentrated under reduced pressure and purified by silica gel column chromatography (elution solvent; normal hexane:isopropyl ether 7:3→0:10) (yield; 16.2 g). To 5.2 g of this product, 100 ml of dimethoxymethane was added, and 1.5 g of phosphorus pentoxide was slowly added at room temperature while stirring, followed by continued stirring for 16 hours. After completion of the reaction, 200 ml of water and 100 ml of ethyl acetate were added thereto, and liquid-liquid extraction was performed. The ethyl acetate layer was removed, dried over sodium sulfate, and then concentrated under reduced pressure. The resultant concentrate was purified by silica gel column chromatography (elution solvent; normal hexane:isopropyl ether 10:0→5:5), to obtain 1,3-dibenzoyloxy-2-methoxymethyloxypropane. This was dissolved in 10 ml of anhydrous acetic acid, 0.1 ml of a boron trifluoride-ether complex was added thereto, and the mixture was allowed to react for one hour at room temperature. The reaction mixture was washed four times with 200 ml of a saturated aqueous solution of sodium carbonate, concentrated under reduced pressure, and then purified by silica gel column chromatography, to obtain 5.1 g of 2-acetoxymethoxy-1,3-dibenzoyloxypropane.

5.7 g of 2-nitroimidazole was weighed, and 10 ml of bistrimethylsilylacetamide was added thereto, to trimethylsilylate the hydrogen at the 1-position. Excess bistrimethylsilylacetamide and the reaction residues were removed under reduced pressure, 30 ml of acetonitrile was added to the remaining, and 3 g of the 2-acetoxymethoxy-1,3-dibenzoyloxypropane was further added to the remaining. While stirring the system at room temperature, 5 ml of stannic chloride was added dropwise, and the mixture was continuously stirred for one hour. The reaction mixture was concentrated under reduced pressure, and then was poured onto a saturated aqueous solution of sodium hydrogen carbonate in ice. 200 ml of ethyl acetate was added to the resultant, liquid-liquid extraction was performed three times, and the ethyl acetate phase was collected and washed with water. The ethyl acetate phase was then concentrated under reduced pressure, and was purified by silica gel column chromatography (elution solvent; chloroform:methanol=100:0→8:2). The reaction mixture was treated in ammonia-saturated anhydrous methanol, and the benzoyl protective group was removed. The resultant was concentrated under reduced pressure, and then was subjected to recrystallization from 2-propanol, to obtain 1-(2-hydroxy-1-hydroxymethyl)ethyl-2-nitroimidazole. This was dissolved in 100 ml of DMF and 20 ml of triethylamine, and 12 g of anhydrous acetic acid dissolved in 100 ml of DMF was added dropwise under ice cooling. The temperature of the system was increased to room temperature, and the system was allowed to react for one hour at room temperature. The reaction mixture was poured onto a saturated aqueous solution of sodium hydrogen carbonate, 200 ml of ethyl acetate was added, and the mixture was washed three times with a saturated aqueous solution of sodium hydrogen carbonate and washed with water. The resultant was concentrated under reduced pressure, and was purified by silica gel column chromatography (elution solvent; chloroform:methanol=100:0→10:90), to obtain 1.3 g (yield with respect to 2-nitroimidazole: 21%) of 1-(1-acetyloxymethyl-2-hydroxyethyl)oxymethyl-2-nitroimidazole. This was analyzed under the following HPLC conditions, and in addition to the main peak (area ratio 98%), the peak for 1-(2-hydroxy-1-hydroxymethyl)ethyl-2-nitroimidazole (area ratio 1.7%) and the peak for 1-(2-benzoyloxy-1-benzoyloxymethyl)ethyl-2-nitroimidazole (area ratio 0.14%), these substances being raw materials, were also recognized.

HPLC conditions; column: ODS 4.6 mm×150 mm, column temperature: 40° C., mobile phase: aqueous solution of acetonitrile 5%→50% (linear gradient, 1 hour), flow rate: 1 ml/min, detection: ultraviolet region 320 nm 117 mg of the thus-obtained 1-[1-acetoxymethyl-2-(hydroxy)ethoxy]methyl-2-nitroimidazole was placed in a flask together with dry pyridine, and 252 mg of toluenesulfonyl chloride was added. The mixture was stirred for 5 hours at room temperature. The reaction mixture was extracted with 30 ml of added ethyl acetate, and the obtained extract was subjected to partition and water washing, two times with 30 ml of water. The organic phase was dried over sodium sulfate, subsequently concentrated under reduced pressure, and purified by silica gel column chromatography, to obtain 1-[1-acetoxymethyl-2-mesylethoxy]methyl-2-nitroimidazole. 10 ml of dry DMF was added to dissolve the product, and the solution was added to a mixture which had been prepared by mixing 10 ml of acetonitrile and 1 ml of water in advance, adding 33.8 mg of potassium fluoride and 80 mg of 18-crown-6, and drying under reduced pressure. The resulting mixture was heated at 110° C. for 8 hours. To the obtained reaction mixture, 20 ml of ethyl acetate was added, and the mixture was washed with 20 ml of water. The aqueous phase was extracted two times with 20 ml of ethyl acetate, and the obtained extract was combined with the organic phase and dried to solid under reduced pressure. The dried product was purified by preparative high performance chromatography, to obtain 15.4 mg of 1-(1-hydroxymethyl-2-fluoro)ethoxymethyl-2-nitroimidazole. From the mass analysis results for this product, M+1(219) was recognized, and thus the structure was confirmed. Also, the elemental analysis values resulted in 38.55% of carbon, 4.11% of hydrogen, 19.28% of nitrogen, and 8.70% of fluorine, thus supporting the structure.

Example 1

According to the method of the present invention, 1-(1-benzoyloxymethyl-2-hydroxyethyl)oxymethyl-2-nitroimidazole was produced. That is, 9.2 g of glycerin was dissolved in 100 ml of chloroform, 50 ml of triethylamine was added, and under ice cooling, 14 g of benzoyl chloride was dissolved in 50 ml of chloroform and added dropwise to the above-obtained mixture while stirring. After completion of the dropwise addition, the mixture was returned to room temperature, and stirring was continued for one hour at room temperature. 100 ml of water was added to wash the mixture with water, and then the mixture was concentrated under reduced pressure and purified by silica gel column chromatography (elution solvent; isopropyl ether:methanol 10:0→7:3) (yield; 14.1 g). To 9 g of this product, 100 ml of dimethoxymethane was added, and 1 g of phosphorus pentoxide was slowly added at room temperature while stirring. The mixture was allowed to react continuously for 16 hours. After completion of the reaction, 200 ml of water and 100 ml of ethyl acetate were added thereto, and liquid-liquid extraction was performed. The ethyl acetate layer was dried over sodium sulfate, and then concentrated under reduced pressure. The resultant concentrate was purified by silica gel column chromatography (elution solvent; normal hexane: isopropyl ether 10:0→5:5), to obtain 9.8 g of 4-benzoyloxymethyl-1,3-dioxolane.

5.7 g of 2-nitroimidazole was weighed, and 10 ml of bistrimethylsilylacetamide was added thereto, to trimethylsilylate the hydrogen at the 1-position. Excess bistrimethylsilylacetamide and the reaction residues were removed under reduced pressure, 30 ml of acetonitrile was added to the remaining, and 4.4 g of 4-benzoyloxymethyl-1,3-dioxolane was further added to the remaining. While stirring the system under ice cooling, 1 ml of a boron trifluoride-ether complex was added dropwise, and the mixture was returned to room temperature, and was allowed to react continuously for 4 hours. After completion of the reaction, the system was concentrated under reduced pressure, 200 ml of ethyl acetate and 200 ml of a saturated aqueous solution of sodium hydrogen carbonate were added thereto, and liquid-liquid extraction was performed. The ethyl acetate layer was taken, and then was washed with 200 ml of water. The resultant was concentrated under reduced pressure, and then was purified by silica gel column chromatography, to obtain 3.2 g of 1-(1-benzoyloxymethyl-2-hydroxyethyl)oxymethyl-2-nitroimidazole. This was analyzed under the following HPLC conditions, and no other peak was recognized in addition to the main peak (are a ratio 99.9%). It was found that in the method of the present invention, the number of steps is smaller, the yield is good, and the purity is also enhanced, as compared to conventional methods.

160 mg of the thus-obtained 1-(1-benzoyloxymethyl-2-hydroxyethyl)oxymethyl-2-nitroimidazole was subjected to mesylation, followed by the operations of fluorination and deprotection, to obtain 18.6 mg of 1-(1-hydroxymethyl-2-fluoro)ethoxymethyl-2-nitroimidazole. From the mass analysis results for this product, M+1(219) was recognized, and thus the structure was confirmed. Also, the elemental analysis values resulted in 38.546 of carbon, 4.12% of hydrogen, 19.27% of nitrogen, and 8.72% of fluorine, thus supporting the structure. It was also found that the rate of fluorination is superior to that of the Reference Example.

INDUSTRIAL APPLICABILITY

The present invention can be applied to the production of a PET imaging agent or the like.

The invention claimed is:

1. A method for producing 1-(1-benzoyloxymethyl-2-hydroxyethyl)oxymethyl-2-nitroimidazole, comprising:
   (A) reacting glycerin with a benzoylating agent to obtain 1-O-benzoylglycerin;
   (B) reacting 1-O-benzoylglycerin with dimethoxymethane in the presence of a dehydrating agent to obtain 4-benzoyloxymethyl-1,3-dioxolane; and then
   (C) reacting 4 benzoyloxymethyl-1,3-dioxolane with 2-nitroimidazole or 2-nitro-1-trialkylsilylimidazole in the presence of a Lewis acid, to obtain 1-(1-benzoyloxymethyl-2-hydroxyethyl)oxymethyl-2-nitroimidazole.

2. The method according to claim 1, wherein the benzoylating agent is benzoyl halide.

3. The method according to claim 1, wherein the dehydrating agent is phosphorus pentoxide.

4. A method for producing 1-(1-hydroxymethyl-2-fluoro)ethoxymethyl-2-nitroimidazole, comprising:
   (D) subjecting the 1-(1-benzoyloxymethyl-2-hydroxyethyl)oxymethyl-2-nitroimidazole obtained by the method according to any one of claims 1 to 3, to substituted sulfonylation, fluorination, and then debenzoylation.

5. The method according to claim 4, wherein a fluorine atom is $^{18}F$ in the fluorination.

6. The method according to claim 1, wherein the benzoylating agent comprises benzoyl chloride.

7. The method according to claim 1, wherein the benzoylating agent comprises benzoyl bromide.

8. The method according to claim 1, wherein the benzoylating agent comprises benzoic acid.

9. The method according to claim 1, wherein the reacting (A) is carried out in the presence of an alkali.

10. The method according to claim 9, wherein the alkali comprises an organic amine.

11. The method according to claim 9, wherein the alkali comprises a carbonate.

12. The method according to claim 1, wherein the reacting (A) is carried out in a range from 0 to 60° C.

13. The method according to claim 1, wherein the dehydrating agent comprises phosphorous oxychloride.

14. The method according to claim 1, wherein, in the reacting (B), the dimethoxymethane is present in a ten-fold molar amount or more relative to 1-O-benzoylglycerin.

15. The method according to claim 1, further comprising, after the reacting (B):
   distilling the 4-benzoyloxymethyl-1,3-dioxolane.

16. The method according to claim 1, wherein the reacting (B) is carried out for at least three hours.

* * * * *